United States Patent [19]

Sugiyama et al.

[11] Patent Number: 5,232,853
[45] Date of Patent: Aug. 3, 1993

[54] METHOD FOR PRODUCING (2R,3S)-3-HYDROXY-2-METHYLBUTYRATE BY MICROBIAL REDUCTION

[75] Inventors: Yoshio Sugiyama, Takasago; Hiroyuki Miya, Ikeda; Mitsuru Kawada, Amagasaki, all of Japan

[73] Assignee: Takeda Chemical Industries, Ltd., Osaka, Japan

[21] Appl. No.: 651,417

[22] PCT Filed: Dec. 17, 1990

[86] PCT No.: PCT/JP90/01643

§ 371 Date: Feb. 7, 1991

§ 102(e) Date: Feb. 7, 1991

[87] PCT Pub. No.: WO91/09959

PCT Pub. Date: Jul. 11, 1991

[30] Foreign Application Priority Data

Dec. 28, 1989 [JP] Japan ................ 1-339965

[51] Int. Cl.$^5$ ................ C12P 7/42
[52] U.S. Cl. ................ 435/280; 435/146
[58] Field of Search ............ 435/280, 135, 136, 141, 435/146

[56] References Cited

U.S. PATENT DOCUMENTS 4,734,367 3/1988 Leuenberger et al. ............ 435/135
5,026,642 6/1991 Radunz et al. ................ 435/117
5,065,761 11/1991 Schneider et al. .............. 435/135

FOREIGN PATENT DOCUMENTS

WO-A1-
9009433 8/1990 European Pat. Off. .

OTHER PUBLICATIONS

Chemical Abstracts, vol. 108, No. 9, Feb. 29, 1988, (Columbus, Ohio, US), Buisson, Didier et al.: "New chiral building blocks by microbial asymmetricreduction: a direct access to functionalized 2R,3R- and 2S,3R-2-methyl-3-hydroxy butyrate synthons", see p. 341, abstract 71630q, & Tetrahedron Lett. 1987, 28(42), 5033-5036.

Chemical Abstracts, vol. 100, No. 17, Apr. 23, 1984, (Columbus, Ohio, US), Akita, Hiroyuki et al.: "The use of microorganisms in organic synthesis. I. Microbiological asymmetric reduction of 2-methyl-3-oxo=butyrates", see p. 504, abstract 137316k, & Chem.Pharm.Bull. 1983, 31(12), 4376-4383.

Chemical Abstracts, vol. 103, No. 25, Dec. 23, 1985, (Columbus, Ohio, US), Furuichi, Akiya et al.: "Enzymes producing two chiral centers. Part I. Purification and properties of an asymmetric reduction enzyme of 2-methyl-3-oxobutyrate in bakers' yeast.", see p. 401, abstract 209519r, & Agric.Biol.Chem. 1985, 49(9), 2563-2570.

Simon, H. et al., Stud. Org. Chem. 13:207-27 (1983).
Crout, D. et al., Eur. J. Biochem. 110:439-444 (1980).

Primary Examiner—Douglas W. Robinson
Assistant Examiner—S. Saucier
Attorney, Agent, or Firm—Wenderoth, Lind & Ponack

[57] ABSTRACT

A (2R,3S)-3-hydroxy-2-methylbutyrate is efficiently and selectively produced by microbial asymmetric reduction of a 2-methyl-3-oxobutyrate with a bacterial strain or its processed material.

10 Claims, No Drawings

METHOD FOR PRODUCING (2R,3S)-3-HYDROXY-2-METHYLBUTYRATE BY MICROBIAL REDUCTION

TECHNICAL FIELD

The present invention relates to a process for producing optically active 3-hydroxy-2-methylbutyrates which are useful starting materials for synthesis of good ferroelectric liquid crystal compounds and the like.

Namely, when 2-methyl-3-oxobutyrates of the formula:

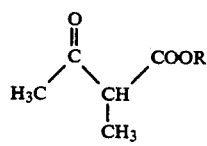

wherein R is an ester forming group, is reduced according to an ordinary chemical method, for example, by using $NaHB_4$, the following four stereomers are formed due to asymmetric carbon atoms at 2- and 3-positions.

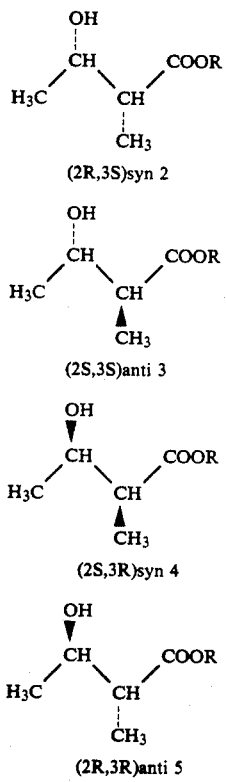

wherein, R is as defined above and the symbol in the parentheses represents the absolute configuration of the asymmetric carbon atoms at 2- and 3-positions. Among these four stereomers, the present invention relates to a process for the selective production of the (2R, 3S)syn 2 isomers of the formula (2) by microbial asymmetric reduction. The isomer of the formula (2) are highly applicable to synthesis of good ferroelectric liquid crystal compounds as starting materials.

BACKGROUND ART

Known processes for producing optically active 3-hydroxy-2-methylbutyrates from 2-methyl-3-oxobutyrates of the formula (1) by microbial asymmetric reduction include the processes using baker's yeast [A. Furuichi et al., Agric. Biol. Chem., 49, 9, 2563-2570 (1985); K. Nakamura et al., Tetrahedron Letters, 27, 3155 (1986); and K. Nakamura et al., Bull. Chem. Soc. Jpn., 62, 1179 (1989)] and the process using other yeast such as *Candida albicans* [H. Akita et al., Chem. Pharm. Bull., 31, 4376 (1983)]. However, these processes are not industrially advantageous processes in view of their low diastereomer selectivity and/or enantiomer selectivity. Further, microbial asymmetric reduction of 2-methyl-3-oxobutyrates with bacteria has not been known heretofore in the prior art.

OBJECTS OF THE INVENTION

The main object of the present invention is to provide a process for selectively and efficiently producing optically active 3-hydroxy-2-methylbutyrates of the formula (2), which are useful starting materials for synthesis of good ferroelectric liquid crystal compounds, polyoxoantibiotics, various naturally occurring physiologically active substances and the like, from the corresponding 3-oxo esters of the formula (1) by using microorganisms, particularly, bacteria.

This object as well as other objects and advantages of the present invention will become apparent to those skilled in the art from the following description.

SUMMARY OF THE INVENTION

The present inventors have found that microbial asymmetric reduction of 2-methyl-3-oxobutyrates of the formula (1) can be efficiently conducted by using bacteria to form the desired optically active 3-hydroxy isomers.

Namely, according to the present invention, there is provided a process for producing a (2R,3S)-3-hydroxy-2-methylbutyrate of the formula (2) which comprises subjecting a 2-methyl-3-oxobutyrate of the formula (1) to asymmetric reduction with a bacterial strain or its processed material.

DISCLOSURE OF THE INVENTION

In the process of the present invention, the ester forming group represented by R in the 2-methyl-3-oxobutyrate of the formula (1) used as the starting material is not specifically limited. For example, R may be lower alkyl, alkoxyalkyl or aralkyl. Examples of lower alkyl include alkyl having 1 to 6 carbon atoms such as methyl, ethyl, propyl, isopropyl, butyl, isobutyl, sec-butyl, tert-butyl, pentyl, neopentyl, hexyl and the like. Examples of alkoxyalkyl include alkoxyalkyl having 3 to 6 carbon atoms such as methoxyethyl, ethoxyethyl, butoxyethyl and the like. Examples of aralkyl include phenyl(lower)alkyl such as benzyl, phenethyl, 1-methylbenzyl, 1-ethylbenzyl, 1-methylphenethyl, 2-methylphenethyl, 2-ethylphenethyl and the like. Among them, ethyl 2-methyl-3-oxobutyrate, isobutyl 2-methyl-3-oxobutyrate, butoxyethyl 2-methyl-3-oxobutyrate and benzyl 2-methyl-3-oxobutyrate are preferred. Particularly, ethyl 2-methyl-3-oxobutyrate is preferred from a practical point of view.

Although the formula (1) represents the keto tautomer, the compounds of the formula (1) can also be in the enol tautomer. The term "2-methyl-3-oxobutyrate" used herein includes each of these tautomers as well as a mixture thereof.

The bacteria used for the asymmetric reduction reaction of the present invention are not specifically limited in so far as they have capability of asymmetric reduction. Examples thereof include bacteria belonging to genera Enterobacter, Erwinia, Escherichia, Klebsiella, Proteus, Salmonella, Serratia, Bacillus and Pediococcus. Any strain newly isolated from soil, food, animal, vegetable or the like can be used in so far as it is capable of producing the compound of the formula (2) from the compound of the formula (1) by asymmetric reduction. Further, the strain may be a mutant obtained by artificial mutagenesis by means of ultraviolet irradiation or treatment with a mutagenic agent, or other bacterial cells integrating an artificially isolated gene fragment necessary for expression of the corresponding reduction activity.

Specific examples of the bacterial strains used for asymmetric reduction of 2-methyl-3-oxobutyrates of the formula (1) include *Enterobacter aerogenes* IFO 13534, *Enterobacter cloacae* IFO 13535, *Erwinia herbicola* IFO 12686, *Escherichia coli* IFO 3549, *Klebsiella pneumoniae* IFO 3319, *Klebsiella terrigena* ATCC 33257 (IFO 14941, FERM BP-2710), *Proteus vulgaris* IFO 3045, *Salmonella typhimurium* IFO 14194, *Serratia grimessii* IFO 13537, *Bacillus pumilus* IFO 12090 and *Pediococcus pentosaceus* IFO 3892. Among these strains, *Klebsiella terrigena* ATCC 33257 is a known strain listed in Catalogue of BACTERIA & BACTERIOPHAGES, Vol. 17 (1989) published by American Type Culture Collection (ATCC), and is readily available from ATCC. This strain has also been deposited at Institute for Fermentation, Osaka (IFO), Japan under the accession number of IFO 14941 since Sep. 14, 1989. Further, it has been deposited at Fermentation Research Institute, Agency of Industrial Science and Technology, Ministry of International Trade and Industry (FRI), Japan according to the Budapest Treaty under the accession number of FERM BP-2710 since Dec. 26, 1989. The other strains are also known strains listed in LIST OF CULTURES, Vol. 8 (1988) published by IFO, and are readily available from IFO.

For conducting the process of the present invention, firstly, these bacterial strains are cultivated.

The cultivation of these strains can be conducted continuously or intermittently by means of normal stationary culture, shaking or agitating culture, submerged culture or solid culture. Culture media to be used may be those having normal compositions in which the bacteria used can be grown. As carbon sources, assimilable materials can be appropriately selected from carbohydrates, fatty acids, organic acids, alcohols and the like. They can be used alone or in combination thereof. Nitrogen sources include organic nitrogen sources such as peptone, yeast extract, meat extract, malt extract, corn steep liquor, soybean flour, urea and the like, as well as inorganic nitrogen sources such as ammonium sulfate, ammonium chloride, ammonium nitrate, ammonium phosphate and the like. They are used alone or in combination thereof as occasion demands. In addition to these carbon and nitrogen sources, preferably, essential growth factors and growth promoters such as minerals, amino acids, vitamins and the like which are necessary for growth of the bacterial strains are added to the culture media.

An aqueous caustic alkali solution, an aqueous sodium carbonate solution or a calcium salt can be appropriately added to control pH during the cultivation. Further, it is advantageous to use an anti-foaming agent to control bubbling. Furthermore, it is also advantageous to aerate nitrogen gas or carbon dioxide gas to bring about anaerobic atmosphere depending upon the bacteria used.

Then, the cultivated strain or its processed material is brought into contact with the compound of the formula (1) to conduct the microbial asymmetric reduction.

As the bacterial strain, the resulting culture as it is or bacterial cells isolated by suitable means such as centrifugation, precipitation, agglutination, filtration through porous membrane, polymer membrane, ceramic membrane, etc. or the like can be used for the asymmetric reduction reaction.

The "processed material" used in the present invention includes masticated cells having capability of asymmetric reduction of the compounds of the formula (1) obtained by various physicochemical methods, for example, sonication, French press, osmotic pressure, freeze-thawing, freeze-drying, alumina grinding and treatment with a lytic enzyme, a surfactant, an organic solvent and the like. The processed material also includes crude or purified enzymes contained in these cells and masticated cells obtained by purification thereof according to the methods described hereinafter. The enzymes can be solubilized by subjecting the above-obtained cells to physicochemical treatment, for example, freeze-thawing, grinding, sonication, dissolution of cell wall membrane, a surfactant or the like. The solubilized enzymes can be purified by further subjecting them to one or more conventional enzyme purification operations such as treatment with protamin, salting out, treatment with an organic solvent, isoelectric point precipitation, ion exchange chromatography, gel filtration, affinity chromatography, crystallization and the like. The enzymes thus obtained can be immobilized by inclusion in natural polymers such as alginate, carrageenan and the like, or synthetic polymers such as polyacrylamide, urethane resin and the like, or immobilized by binding to carriers such as activated charcoal, ceramic, dextran, agarose materials, porous glass, ion exchange resin and the like.

For conducting the asymmetric reduction reaction by bringing the compound of the formula (1) into contact with a culture of the bacterial strain or its processed material, the compound of the formula (1) is preferably used in an concentration of 0.1 to 5% by weight, more preferably, 0.2 to 3% by weight. Further, it is desirable to add a carbon source assimilable by the bacterial strain (e.g., carbohydrate, fatty acid, organic acid, alcohol) as a hydrogen donor together with the compound of the formula (1). In order to promote the reaction, minerals and vitamins can also be added.

The reaction temperature is not limited to a specific range in so far as the asymmetric reduction can proceed. Preferably, the reaction temperature is in the range of 20° to 60° C., more preferably, 25° to 50° C. The pH range varies depending upon a particular bacterial strain used. When a bacterial strain belonging to the genus Pediococcus is used, pH 3 to 7 is preferred. When other bacterial strains are used, pH 5 to 9 is preferred. For efficient progress of the reduction reaction, preferably, the reaction mixture is suitably agitated. However, when a bacterial strain belonging to the genus Pediococcus is used, it is preferable to maintain anaerobic atmosphere. For this purpose, nitrogen gas or carbon dioxide gas can be aerated. On the other hand, when other bacterial strains are used, it is preferable to conduct the reaction under sufficient aerobic conditions.

The reaction is continued until the asymmetric reduction of the compound of the formula (1) is completed. Normally, it takes about 8 to 96 hours.

After the reaction, the optically active 3-hydroxy isomer thus formed can be readily recovered and collected by one or more known purification methods such as extraction, concentration and the like.

The compound of the formula (2) thus obtained by the process of the present invention can be converted into the corresponding 3-alkoxy-2-methylbutyrate by known alkylation of the hydroxy group followed by hydrolysis. Then, the 3-alkoxy-2-methylbutyrate is condensed with a side chain component containing no chiral center (or a side chain component containing a chiral center), whereby a good ferroelectric liquid crystal compound having excellent liquid crystal properties can be readily synthesized (e.g., EP-A-322862).

As described hereinabove, according to the process of the present invention, (2R,3S)-3-hydroxy-2-methylbutyrates which are useful starting materials for the production of good ferroelectric liquid crystal compounds and the like can be readily and efficiently produced.

The following examples and reference example further illustrate the present invention in detail but are not to be construed to limit the scope thereof.

EXAMPLE 1

The following reduction reaction was conducted by using ethyl 2-methyl-3-oxobutyrate as the substrate and the ten strains shown in Table 1.

A bouillon slant culture of each strain was inoculated into a 200 ml Erlenmeyer flask containing a sterilized seed culture medium (20 ml) composed of Bacto tryptone 1%, Bacto yeast extract 0.5%, NaCl 0.5% and glucose 1%, and cultivated on a rotary shaker at 200 rpm at 28° C. for 16 hours. The seed culture solution (each 0.3 ml portion) was transferred to 200 ml ribbed Erlenmeyer flasks containing a sterilized main culture medium (pH 7, 30 ml) composed of meat extract 1%, polypeptone 1%, NaCl 0.5%, $CaCO_3$ 4% and glucose 2% (separately sterilized) and cultivated with shaking at 200 rpm at 30° C. After 24 hours from the initiation of the cultivation, the substrate (120 mg) and glucose (1.2 g) were added to each flask and the cultivation was continued for additional 24 hours under the same conditions as those of the cultivation of the main culture. After completion of the reaction, the reaction mixture was extracted twice with the same volume (30 ml) of ethyl acetate and the combined ethyl acetate layer was washed with water, dehydrated and adjusted to a predetermined volume. A part of the extract was taken as a sample and the yield of the reduced product and syn/anti ratio were determined by gas chromatography as described hereinafter. On the other hand, the remaining extract was concentrated under reduced pressure. The resulting concentrate was dissolved in a small amount of ether and subjected to Kugel distillation to obtain a colorless oily reduction product. The optical purity (enantiomeric excess) was determined by high performance liquid chromatography as described hereinafter.

The results are shown in Table 1. In each strain, diastereomer and enantiomer selectivity is higher than that obtained in known microbial asymmetric reduction using baker's yeast.

The analytical method and conditions used are as follows:

(1) Gas chromatography

Hitachi G-3000 gas chromatograph was used. Gas chromatography was conducted by using nonyl alcohol as an internal standard and chemically synthesized ethyl (2R, 3S)-and (2S, 3S)-3-hydroxy-2-methylbtyrates as authentic samples under the following conditions:

column: ULBON-20M (0.25 mm×25 m)
column temperature: 110° C.
carrier gas: He
detection: FID (2) High performance liquid chromatography Waters 600-E high performance liquid chromatograph was used. High performance liquid chromatography was conducted by using chemically synthesized four stereomers of ethyl 3-hydroxy-2-methylbutyrate as authentic samples under the following conditions:

column: Chiralcell OB (4.6 mm×250 mm), two columns
column temperature: 25° C.
eluent: hexane:2-propanol (99.5:0.5)
flow rate: 1.0 ml/min.
detection: UV 220 nm

TABLE 1

| Strains | Reduction yield (%) | syn/anti ratio | Optical purity (% ee*) |
|---|---|---|---|
| Enterobacter aerogenes IFO 13534 | 84 | 98/2 | syn 2 > 99 |
| Enterobacter cloacae IFO 13535 | 95 | 99/1 | syn 2 > 99 |
| Erwinia herbicola IFO 12686 | 84 | 98/2 | syn 2 > 99 |
| Escherichia coli IFO 3549 | 95 | 99/1 | syn 2 > 99 |
| Klebsiella pneumoniae IFO 3319 | 99 | 98/2 | syn 2 > 99 |
| Klebsiella terrigena ATCC 33257 (IFO 14941, FERM BP-2710) | 95 | 99/1 | syn 2 > 99 |
| Proteus vulgaris IFO 3045 | 99 | 96/4 | syn 2 > 99 |
| Salmonella typhimurium IFO 14194 | 83 | 96/4 | syn 2 > 99 |
| Serratia grimessii IFO 13537 | 85 | 96/4 | syn 2 > 99 |
| Bacillus pumilus IFO 12090 | 38 | 98/2 | syn 2 > 99 |

*ee: enantiomeric excess

EXAMPLE 2

Pediococcus pentosaceus IFO 3892 strain grown by stab culture in commercially available GAM agar medium (manufactured by Nissui Seiyaku Kabushiki Kaisha, Japan) was inoculated in a 200 ml Erlenmeyer flask containing a sterilized seed culture medium (pH 6.6, 30 ml) composed of glucose 2%, polypeptone 1%, yeast extract 0.5%, meat extract 1%, Tween 80 0.1%, sodium acetate 0.3%, triammonium citrate 0.2%, $MgSO_4.7H_2O$ 0.02% and $MnSO_4.4-6H_2O$ 0.005% and cultivated by stationary culture at 30° C. for 24 hours. This seed culture solution (each 1.5 ml portion) was transferred to 200 ml ribbed Erlenmeyer flasks containing a sterilized fermentation culture medium (pH 6.6, 30 ml) having the same composition as that of the seed culture medium except that $CaCO_3$ 1% was further added, and cultivated by stationary culture at 30° C. After 24 hours from the initiation of the cultivation, ethyl 2-methyl-3-oxobutyrate (60 mg) and glucose (1.2 g) were added to each flask. After replacing the gaseous phase by nitrogen gas, the reaction system was sealed and the reaction was conducted with shaking at 200 rpm at 30° C. for 24 hours. After completion of the reaction, the reduction product was analyzed according to the same manner as that described in Example 1. As a result, the reduction yield was 30%, syn/anti ratio was 97:3 and optical purity of syn 2 isomer was more than 99% ee.

EXAMPLE 3

*Klebsiella pneumoniae* IFO 3319 was cultivated according to the same manner as that described in Example 1. After 24 hours from the initiation of the cultivation of the main culture, each of five substrates shown in Table 2 (120 mg) and glucose 1.2 g were added to respective flasks and the reaction was conducted for 24 hours under the same conditions as those of the cultivation of the main culture. After completion of the reaction, each reaction mixture was extracted twice with the same volume (30 ml) of ethyl acetate. The combined ethyl acetate layer was washed with water, dehydrated and adjusted to a predetermined volume. A part of the extract was subjected to gas chromatography as described in Example 1. The resulting chromatogram was compared with that obtained by separately reducing the same substrate with baker's yeast to identify the peaks of the syn and anti isomers. Further, the syn/anti ratio was calculated by the area ratio of both peaks. On the other hand, the remaining extract was concentrated under reduced pressure. The concentrate was dissolved in a small amount of ether and subjected to Kugel distillation to obtain a colorless oily reduction product. The reduction product was dissolved in ethanol (8 ml) and the strong basic anion exchange resin, Amberlite IRA 402 (manufactured by Rohm and Haas Co., U.S.A., 0.4 ml) was added thereto. The mixture was stirred at room temperature for 48 hours to conduct the ester interchange reaction. The resulting ethyl ester was isolated and determined by high performance liquid chromatography described in Example 1 to calculate the enantiomeric excess ratio. The optical purity was expressed by this ratio. The results are shown in Table 2.

TABLE 2

| Substrate (R) | Reduction* yield (%) | syn/anti ratio | Optical purity (% ee) |
|---|---|---|---|
| isobutyl —CH$_2$CH(CH$_3$)$_2$ | 98 | 98/2 | syn 2 > 99 |
| neopentyl —CH$_2$C(CH$_3$)$_3$ | 94 | 98/2 | syn 2 > 99 |
| n-hexyl —C$_6$H$_{13}$ | 45 | 95/5 | syn 2 > 99 |
| 2-butoxyethyl —CH$_2$CH$_2$OC$_4$H$_9$ | 95 | 97/3 | syn 2 > 99 |
| benzyl | 91 | 96/4 | syn 2 > 99 |

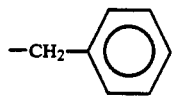

* $\dfrac{\text{Amount of substrate used} - \text{Amount of remaining substrate}}{\text{Amount of substrate used}} \times 100$

EXAMPLE 4

According to the same manner as that described in Example 1, a seed culture solution of *Klebsiella pneumoniae* IFO 3319 was prepared. The 20 ml portion of this culture solution was transferred to a 5 liter jar fermenter containing a sterilized main culture medium (pH 7, 2 liters) composed of meat extract 1%, polypeptone 1%, NaCl 0.5% and an anti-foaming agent 0.05% and glucose 2% (separately sterilized) and cultivated at 30° C. by submerged culture with stirring at 800 rpm and aeration rate of 0.6 liter/min. When the pH of the culture solution was dropped below 6.5 during the cultivation, an aqueous 15% (w/v) sodium hydroxide solution was added to maintain the pH at 6.5. After 18 hours from the initiation of the cultivation, ethyl 2-methyl-3-oxobutyrate (35 g) and an aqueous 40% (w/v) glucose solution (200 ml) were added, and the reaction was conducted for 24 hours under the same conditions as those of the cultivation of the main culture. The pH was adjusted according to the same manner as that described above. After completion of the reaction, the reaction mixture (2.18 liters) was extracted once with ethyl acetate (2 liters) and further twice with ethyl acetate (1 liter). The combined ethyl acetate layer was filtered to remove insoluble materials and the filtrate was washed with water and dehydrated. A part of the extract was taken as a sample and it was analyzed by gas chromatography as described in Example 1. As a result, the amount of remaining substrate was 0.5 g, the yield of the reduction product was 34.0 g (reduction yield: 97%) and syn/anti ratio was 99/1. On the other hand, the remaining extract was concentrated under reduced pressure to obtain a concentrate (35.1 g). The concentrate was dissolved in a minimum amount of ether and subjected to Kugel distillation to obtain a colorless oily reduction product (33.5 g). The reduction product was separated and determined by high performance liquid chromatograph as described in Example 1. As a result, the amounts of syn 2, anti 3 and anti 5 formed were 33.0 g, 0.25 g and 0.10 g, respectively. No syn 4 was detected.

EXAMPLE 5

According to the same manner as that described in Example 4, *Klebsiella pneumoniae* IFO 3319 was cultivated to obtain a main culture (about 2 liters).

i) Extraction of reductase

The main culture (1 liter) was centrifuged at 10,000 × g for 20 minutes to collect cells. The cells were washed once with 10 mM phosphate buffer solution (pH 6.0, about 200 ml, hereinafter merely referred to as buffer) containing 2-mercaptoethanol (5 mM) and phenylmethylsulfonyl fluoride (2 μg/ml) by centrifugation to obtain washed cells (about 30 g, wet weight). All the washed cells were suspended in the buffer and the volume was adjusted to 150 ml with the buffer. Each 50 ml portion of the suspension was sonicated at output of 180 W for 20 minutes. The combined sonicated suspension was centrifuged at 35,500 × g for 20 minutes to obtain a supernatant (145 ml). When the protein concentration of this supernatant was determined by Protein Assay Kit (manufactured by Bio-Rad Inc., U.S.A.) with bovine serum albumin as a standard, it was 33.5 mg/ml. Its activity for reducing ethyl 2-methyl-3-oxobutyrate determined by the method as described hereinafter was 0.30 U/ml.

The enzyme activity was determined as follows:

A reaction mixture having the total volume of 1 ml which was composed of phosphate buffer solution (pH 7.0, 40 μmol), NADPH (0.2 μmol), a substrate (ethyl 2-methyl-3-oxobutyrate, 2 μmol) and an enzyme solution was maintained at 30° C., and the decrease in absorbance at 340 nm was continuously traced. The enzyme activity was expressed by "units (U)" and 1 U was defined as the amount of the enzyme which oxidized 1

μmol of NADPH per 1 minute under the above conditions.

ii) Purification of enzyme

The above supernatant was diluted with the buffer so that the protein concentration became 10 mg/ml and solid ammonium sulfate was added little by little to obtain a 40% saturated solution. The precipitate thus formed was removed by centrifugation and solid ammonium sulfate was further added little by little to obtain a 80% saturated solution. The precipitate thus formed was collected by centrifugation and it was dissolved in the buffer. The volume was adjusted to 55 ml. The solution was dialyzed against the buffer (pH 8.0, 2 liters) at 4° C. for 20 hours with replacing the buffer once with another fresh buffer in the course of the dialysis. Insoluble materials formed during the dialysis were removed by centrifugation to obtain a clear supernatant.

The entire supernatant was applied to TSK-Gel DEAE-5PW column (20×150 mm) equilibrated with 10 mM phosphate buffer solution (pH 8.0) and the column was washed with the same buffer solution (200 ml). The enzyme was eluted with a gradient of sodium chloride in the same buffer solution linearly increasing from 0 to 0.15 M. The active fractions were collected and ammonium sulfate was added thereto to obtain a 90% saturated solution. The precipitate thus formed was recovered by centrifugation.

The precipitate was dissolved in a small amount of 50 mM phosphate buffer solution (pH 7.0) and the solution was adsorbed on a AF-Red Toyopearl column (25×50 mm) equilibrated with the same buffer solution. The enzyme was eluted with a gradient of sodium chloride in the same buffer solution linearly increasing from 0 to 1 M. The active fractions were collected and a precipitate was recovered by ammonium sulfate salting out according to the same manner as that described above.

The precipitate was dissolved in a minimum amount of 50 mM phosphate buffer solution (pH 7.0) containing 0.3 M sodium chloride. The solution was applied to TSK-Gel G 3000 SW column (20×300 mm) equilibrated with the same buffer solution. The column was eluted with the same buffer solution. The protein concentration of the active fraction (13 ml) was 0.52 mg/ml and the enzyme activity was 1.17 U/ml. Accordingly, the recovery of the desired enzyme was about 35% and the purity was about 250 times based on the sonicated extract.

The uniformity of the purified enzyme was confirmed by polyacrylamide gel electrophoresis.

iii) Reduction of ethyl 2-methyl-3-oxobutyrate by purified enzyme

A reaction mixture having the total volume of 4 ml which was composed of phosphate buffer solution (pH 7.0, 400 μmol), ethyl 2-methyl-3-oxobutyrate (200 μmol), glucose (200 μmol), NADPH (0.8 μmol), glucose dehydrogenase (Bacillus sp., manufactured by Sigma, Co., U.S.A., 1 U) and the above purified enzyme (1 U) was reacted with shaking gently for 6 hours, while the temperature was maintained at 30° C. After completion of the reaction, the reaction mixture was extracted twice with the same volume (4 ml) of ethyl acetate. The combined ethyl acetate layer was dehydrated and the volume thereof was adjusted to the predetermined volume. The reduction product in a sample thereof was determined according to the same manner as that described in Example 1. As a result, the amounts of syn and anti isomers formed were 197 and 0.6 μmol, respectively. All the syn isomers are syn 2 and no syn 4 isomer was detected. The turnover number of NADPH under these reaction conditions was about 250.

REFERENCE EXAMPLE

Preparation of 4-[(2R, 3S)-3-methoxy-2-methylbutyryloxy]phenyl 4'-octyloxy-4-biphenylcarboxylate i) Preparation of (2R, 3S)-3-methoxy-2-methylbutyric acid Ethyl (2R, 3S)-3-hydroxy-2-methylbutyrate (8.20 g) and methyl iodate (78.0 g) were dissolved in N,N-dimethylformamide (150 ml). To this solution was added sodium hydride (about 60% in oil, 2.46 g) little by little with ice cooling and the mixture was stirred for 1 hour with ice cooling. The reaction mixture was poured into ethyl acetate (300 ml) and the mixture was stirred for 10 minutes. Insoluble materials were filtered off and the filtrate was washed 3 times with water. The organic layer was dried, concentrated and distilled under reduced pressure (b.p. 80° C./30 mmHg) to obtain ethyl (2R, 3S)-3-methoxy-2-methylbutyrate (6.87 g).

This methyl ether (2.55 g) was dissolved in dioxane (50 ml) and conc. hydrochloric acid (36 %, 10 ml) and water (50 ml) were added to the solution. The solution was heated at 90° C. for 5 hours. The reaction mixture was poured into water (100 ml) and the mixture was extracted 4 times with ethyl acetate. The combined extract was dehydrated, concentrated and distilled under reduced pressure (b.p. 105° C./1 mmHg) to obtain (2R, 3S)-3-methoxy-2-methylbutyric acid (1.49 g).

$^1$H-NMR and IR spectra of this compound are as follows:

$^1$H-NMR (90 MHz, CDCl$_3$) δ: 1.15 (3H, s), 1.23 (3H, s), 2.5–2.8 (1H, m), 3.39 (3H, s), 3.47–3.74 (1H, m), 6.0 (1H, b)

IR $\nu_{max}^{neat}$cm$^{-1}$: 3450, 1710, 1100 ii) Esterification (2R, 3S)-3-methoxy-2-methylbutyric acid prepared in the above i) (0.79 g), 4-hydroxyphenyl 4'-octyloxy-4-biphenylcarboxylate (2.5 g) and tributylamine (2.66 g) were dissolved in dehydrated tetrahydrofuran (40 ml) and 2-chloro-1-methylpyridinium iodide (1.84 g) was added thereto. The mixture was heated under reflux for 7 hours. Insoluble materials were filtered off and the filtrate was concentrated under reduced pressure. The residue was separated and purified by silica gel column chromatography [eluent:chloroform:n-hexane (4:1)] and recrystallized from ethanol to obtain the title compound (0.36 g).

$^1$H-NMR and IR spectra of this compound are as follows:

$^1$H-NMR (90 MHz, CDCl$_3$) δ: 0.90 (3H, t), 1.05–1.6 (16H, m), 1.8 (2H, b), 2.65–2.9 (1H, m), 3.40 (3H, s), 3.6–3.82 (1H, m), 4.01 (2H, t), 6.94–8.25 (12H, m)

IR $\nu_{max}^{KBr}$cm$^{-1}$: 1760, 1730, 1610, 1510, 1100, 830

Elemental analysis for $C_{33}H_{40}O_6$,

Calcd: C, 74.41; H, 7.57.

Found: C, 74.69; H, 7.52.

We claim:

1. A process for producing a (2R, 3S)-3-hydroxy-2-methylbutyrate which comprises subjecting a 2-methyl-3-oxobutyrate to asymmetric reduction with a bacterial strain or a processed material derived therefrom and recovering the (2R, 3S)-3-hydroxy-2-methylbutyrate therefrom, said bacterial strain being selected from the group consisting of *Enterobacter aerogenes, Enterobacter cloacae, Erwinia herbicola, Escherichia coli, Klebsiella pneumoniae, Klebsiella terrigena, Proteus vulgaris, Salmo-* nella typhimurium, Serratia grimessii, Bacillus pumilus and Pediococcus pentosaceus.

2. A process according to claim 1, wherein the bacterial strain is selected from the group consisting of Enterobacter aerogenes IFO 13534, Enterobacter cloacae IFO 13535, Erwinia herbicola IFO 12686, Escherichia coli IFO 3549, Klebsiella pneumoniae IFO 3319, Klebsiella terrigena ATCC 33257 (IFO 14941, FERM BP-2710), Proteus vulgaris IFO 3045, Salmonella typhimurium IFO 14194, Serratia grimessii IFO 13537, Bacillus pumilus IFO 12090 and Pediococcus pentosaceus IFO 3892.

3. A process according to claim 4, wherein the bacterial strain is Klebsiella pneumoniae IFO 3319.

4. A process according to claim 4, wherein the bacterial strain is Klebsiella terrigena ATCC 33257.

5. A process according to claim 13, wherein the processed material is masticated bacterial cells.

6. A process according to claim 13, wherein the processed material is a reductase contained in the bacterial strain.

7. A process according to claim 13, wherein the 2-methyl-3-oxobutyrate is used in a concentration of 0.1 to 5% by weight.

8. A process according to claim 13, wherein asymmetric reduction is conducted at 20° to 60° C.

9. A process according to claim 13, wherein asymmetric reduction is conducted at pH 3 to 9.

10. A process according to claim 13, wherein asymmetric reduction is conducted for 8 to 96 hours.

* * * * *